United States Patent
Buddharaju

(10) Patent No.: US 10,226,377 B2
(45) Date of Patent: Mar. 12, 2019

(54) CONDOM CATHETER

(71) Applicant: Venkata Buddharaju, Park Ridge, IL (US)

(72) Inventor: Venkata Buddharaju, Park Ridge, IL (US)

(*) Notice: Subject to any disclaimer, the term of this patent is extended or adjusted under 35 U.S.C. 154(b) by 190 days.

(21) Appl. No.: 14/964,891

(22) Filed: Dec. 10, 2015

(65) Prior Publication Data

US 2017/0165099 A1    Jun. 15, 2017

(51) Int. Cl.
*A61F 5/44* (2006.01)
*A61F 5/453* (2006.01)
*A61F 5/457* (2006.01)

(52) U.S. Cl.
CPC .......... *A61F 5/453* (2013.01); *A61F 5/4408* (2013.01)

(58) Field of Classification Search
CPC ............................... A61F 5/453; A61F 5/4408
See application file for complete search history.

(56) References Cited

U.S. PATENT DOCUMENTS

| | | | | |
|---|---|---|---|---|
| 1,730,766 A * | 10/1929 | Harrington | ............ | A61F 13/64 604/398 |
| 1,890,482 A * | 12/1932 | Weissberg | ............... | A61J 9/06 215/11.1 |
| 1,917,979 A * | 7/1933 | Kelly | ................... | A61F 13/64 604/397 |
| 1,919,124 A * | 7/1933 | Panullo | ................. | A61F 13/64 604/401 |
| 2,310,505 A * | 2/1943 | Blackburn | ............ | A61F 5/453 119/869 |
| 3,032,038 A * | 5/1962 | Swinn | ...................... | A61F 5/453 604/353 |
| 3,357,430 A * | 12/1967 | Rosenberg | ............ | A61F 5/453 604/353 |
| 3,405,714 A | 10/1968 | Moss | | |
| 3,489,150 A * | 1/1970 | Glaude | .................. | A61F 5/453 604/353 |
| 4,073,295 A * | 2/1978 | Laufbahn | ............... | A61F 5/453 604/353 |

(Continued)

FOREIGN PATENT DOCUMENTS

EP    1570819 B1    4/2011
WO    2009009832 A1    1/2009

OTHER PUBLICATIONS

International Search Report of the International Searching Authority prepared by the USPTO in connection with PCT/US2016/065911, dated Feb. 23, 2017; Entire Document (11 pages).

*Primary Examiner* — Adam Marcetich
(74) *Attorney, Agent, or Firm* — Richard Patent Law P.C.

(57) ABSTRACT

A catheter includes a condom portion including a catheter ring and a tubular portion having a first end and a second end. The first end of the tubular portion is coupled to the catheter ring. The second end of the tubular portion defines an opening. The catheter also includes a flap directly coupled to the catheter ring. The flap includes a slot. The catheter also includes an elastic strap including a first end and a second end. The first end of the elastic strap is directly attachable to the catheter ring. The second end of the elastic strap includes a first portion and a second portion. The first portion is removably attachable to the second portion through the slot.

16 Claims, 3 Drawing Sheets

(56) References Cited

U.S. PATENT DOCUMENTS

| | | | |
|---|---|---|---|
| 4,994,051 A * | 2/1991 | Walsh | A61F 5/453 604/349 |
| 4,997,427 A * | 3/1991 | Bowen | A61F 5/453 604/349 |
| 5,282,557 A * | 2/1994 | McCook | A45F 3/16 222/175 |
| 5,797,890 A | 8/1998 | Goulter et al. | |
| 6,059,762 A | 5/2000 | Boyer et al. | |
| 6,113,582 A | 9/2000 | DWork | |
| 6,152,903 A | 11/2000 | Falconer | |
| 6,443,930 B1 | 9/2002 | Silverstein | |
| 6,558,369 B2 | 5/2003 | Rosenblum | |
| 6,616,024 B1 * | 9/2003 | Perry | A45F 5/00 224/251 |
| 6,635,037 B1 | 10/2003 | Bennett | |
| 6,682,511 B2 | 1/2004 | Besoyan | |
| 6,887,223 B2 | 5/2005 | Bisbee | |
| 7,044,939 B1 | 5/2006 | Fajnszajn | |
| 8,187,238 B1 | 5/2012 | Dupree | |
| 8,672,910 B1 | 3/2014 | Kaufman | |
| 8,986,271 B1 | 3/2015 | Horne | |
| 9,084,470 B1 * | 7/2015 | Huck | A45F 3/14 |
| 2002/0029406 A1 * | 3/2002 | Meyer | A61M 25/02 2/310 |
| 2002/0145026 A1 * | 10/2002 | Perry | A45F 5/00 224/604 |
| 2003/0200937 A1 * | 10/2003 | Muckleroy | A01K 1/029 119/497 |
| 2004/0138623 A1 * | 7/2004 | Rose | A61M 25/02 604/174 |
| 2004/0206792 A1 * | 10/2004 | Mineer | A45C 11/38 224/259 |
| 2005/0101923 A1 | 5/2005 | Elson et al. | |
| 2005/0101924 A1 * | 5/2005 | Elson | A61F 5/453 604/349 |
| 2006/0004332 A1 * | 1/2006 | Marx | A61F 5/453 604/349 |
| 2007/0037483 A1 * | 2/2007 | Huang | A41C 1/10 450/151 |
| 2008/0108864 A1 * | 5/2008 | Girgen | A61F 5/40 600/41 |
| 2008/0183157 A1 | 7/2008 | Walters | |
| 2009/0018530 A1 * | 1/2009 | Nielsen | A61F 5/453 604/544 |
| 2009/0179057 A1 * | 7/2009 | Basye | A45F 3/047 224/628 |
| 2010/0280470 A1 * | 11/2010 | Khoubnazar | A61F 13/471 604/365 |
| 2010/0282808 A1 * | 11/2010 | Debnam | A41D 13/0007 224/637 |
| 2011/0077610 A1 | 3/2011 | Kikumoto et al. | |
| 2011/0087181 A1 | 4/2011 | Bidwell et al. | |
| 2011/0092928 A1 | 4/2011 | Saez | |
| 2012/0267410 A1 * | 10/2012 | Loudenslager | A63B 55/00 224/627 |
| 2014/0018715 A1 * | 1/2014 | Ingimundarson | A61F 5/026 602/19 |
| 2015/0045757 A1 | 2/2015 | Lee et al. | |
| 2015/0257924 A1 | 9/2015 | Siegel | |
| 2015/0290051 A1 | 10/2015 | Gierer | |

* cited by examiner

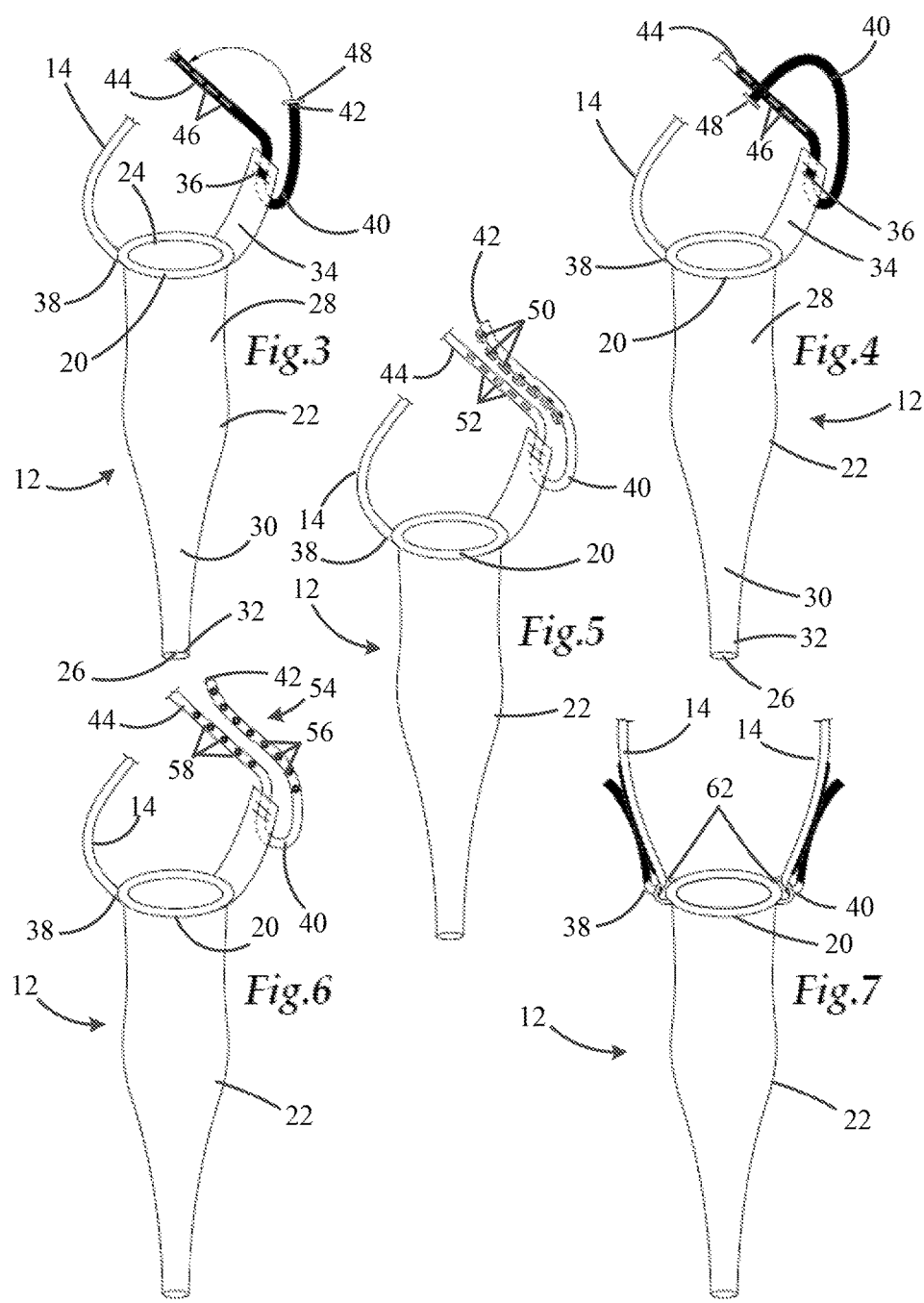

ND CATHETER

BACKGROUND

The present disclosure relates to male catheters.

SUMMARY

In one embodiment, the disclosure provides a catheter including a condom portion including a catheter ring and a tubular portion having a first end and a second end. The first end of the tubular portion is coupled to the catheter ring. The second end of the tubular portion defines an opening. The catheter also includes a flap directly coupled to the catheter ring. The flap includes a slot. The catheter also includes an elastic strap including a first end and a second end. The first end of the elastic strap is directly attachable to the catheter ring. The second end of the elastic strap includes a first portion and a second portion. The first portion is removably attachable to the second portion through the slot.

In another embodiment, the disclosure provides a catheter including a condom portion including a catheter ring and a tubular portion extending from the catheter ring and ending in an opening. The catheter also includes a flap attached to the catheter ring and a strap including a first end attachable to the catheter ring and a second end. The second end of the strap is removably attachable to the flap.

In yet another embodiment, the disclosure provides a catheter including a condom portion including a catheter ring and a tubular portion defining an opening. The catheter also includes an elastic strap including a first end and a second end. The first end of the elastic strap is configured for coupling to the catheter ring. The second end of the elastic strap is configured for coupling to the catheter ring.

Other aspects of the disclosure will become apparent by consideration of the detailed description and accompanying drawings.

BRIEF DESCRIPTION OF THE DRAWINGS

FIG. 3 illustrates a close-up perspective view of the condom catheter of FIG. 1 including a hook and a plurality of openings at the second end of the elastic strap.

FIG. 4 illustrates a close-up perspective view of the condom catheter of FIG. 1 including the hook of FIG. 3 inserted into one of the plurality of openings.

FIG. 5 illustrates a close-up perspective view of the condom catheter of FIG. 1 including a plurality of openings and a plurality of catches at the second end of the elastic strap.

FIG. 6 illustrates a close-up perspective view of the condom catheter of FIG. 1 including a plurality of button snaps at the second end of the elastic strap.

FIG. 7 illustrates a close-up perspective view of a condom catheter according to a third embodiment including Velcro® at a first and a second end of an elastic strap.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of supporting other embodiments and of being practiced or of being carried out in various ways.

Figure 1:
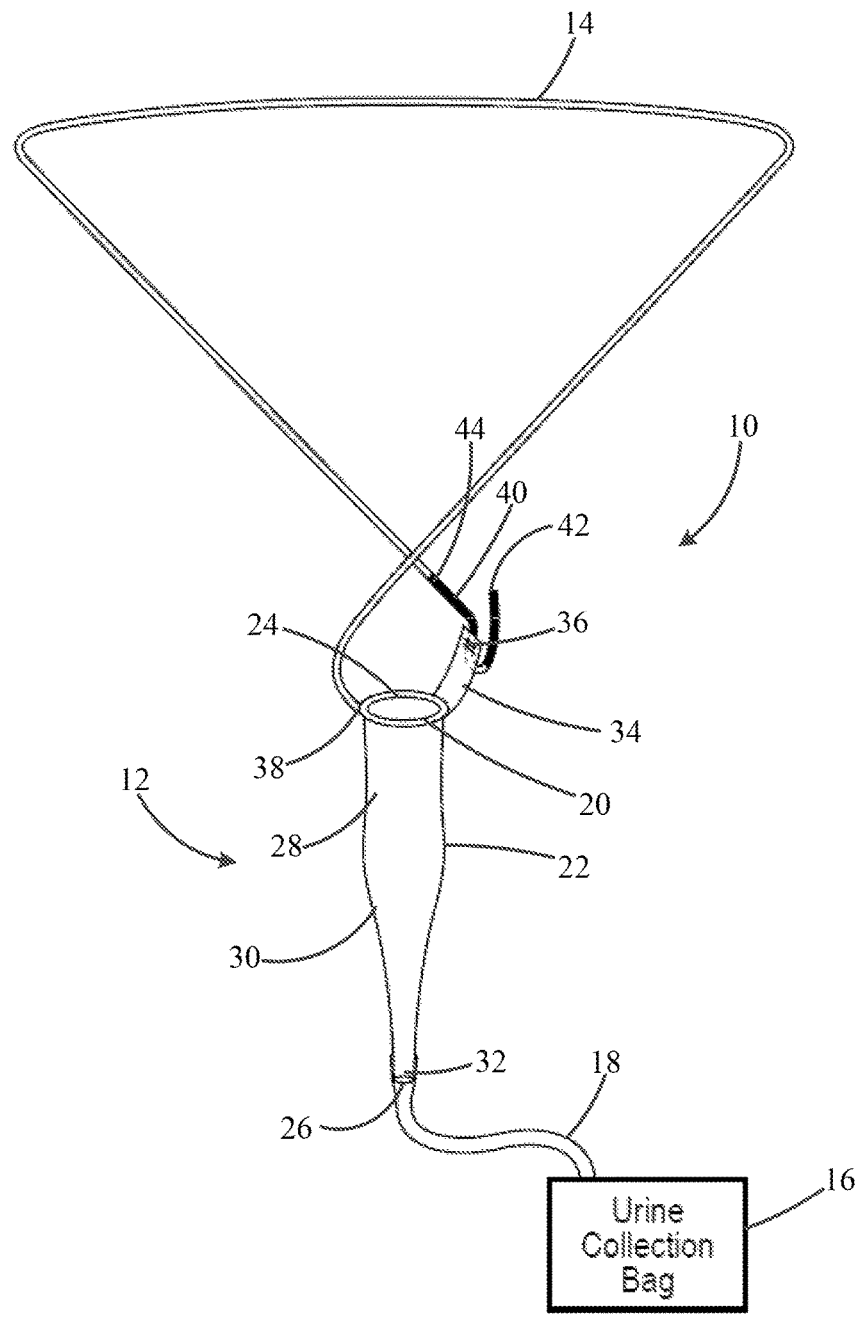
FIG. 1 illustrates a perspective view of a condom catheter according to a first embodiment including Velcro® at a second end of an elastic strap.

FIG. 1 illustrates a condom catheter 10 for a male. The condom catheter 10 includes a condom portion 12 and an elastic strap 14. The condom catheter 10 couples to a urine collection bag 16 by a tube 18 and is configured to collect and send urine from the condom catheter 10 to the urine collection bag 16, as explained in greater detail below.

The condom portion 12 includes a catheter ring 20 and a tubular portion 22. An interior of the catheter ring 20 defines an expandable sphincter 24. The expandable sphincter 24 changes sizes so that the catheter ring 20 may conform to a diameter of a penis P of the patient. The expandable sphincter 24 provides a near liquid-tight seal between the condom portion 12 and the penis P so that urine or other liquids may not easily escape between the penis P and the catheter ring 20. The expandable nature of the sphincter 24 may also provide a comfortable fit for the patient and reduce the incidence of skin irritation as the condom portion 12 does not slide or substantially shift when positioned on the penis P.

Figure 2:
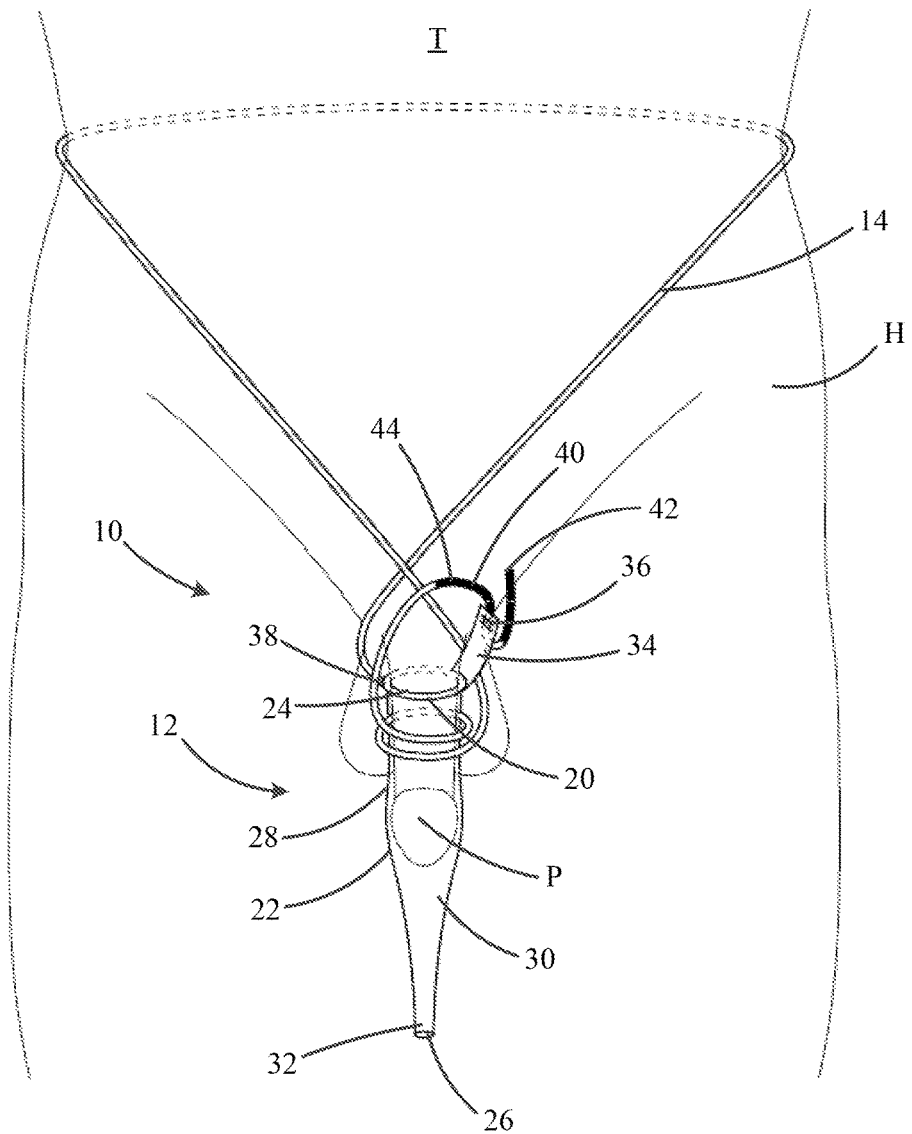
FIG. 2 illustrates a perspective view of a condom catheter according to a second embodiment and as applied.

The tubular portion 22 of the condom portion 12 is directly attached to or otherwise integrally formed as once piece with the catheter ring 20 and extends in an axial direction from the catheter ring 20. The tubular portion 22 may vary in diameter along its length, as illustrated by FIGS. 1-7, so as to more comfortably fit around the penis P and to reduce the potential for liquid to leak from the condom catheter 10. The tubular portion 22 may have a diameter that is the same or nearly the same as the shaft of the penis P at or near the sphincter 24 and slightly increases from the catheter ring 20 so that the condom portion 12 is not tight around the head of the penis P, as illustrated in FIG. 2. The diameter of the tubular portion 22 thereafter decreases and tapers to an opening 26, as illustrated.

The tubular portion 22 may include a soft portion 28 and a firm portion 30. The soft portion 28 is positioned between the firm portion 30 and the catheter ring 20 for patient comfort when the condom catheter 10 is attached for extended periods of time. In general, the soft portion 28 extends from the catheter ring 20 to at or near the point or area at which the diameter of the tubular portion 22 begins to taper. The firm portion 30 extends from that point or area to a tip 32. The tip 32 provides a firm and liquid-tight coupling to the tube 18 and defines an opening 26. In some embodiments, the transition from the soft portion 28 to the firm portion 30 is gradual over a predetermined length of the portion 22. In alternative embodiments, the transition may be abrupt.

In the illustrated embodiment, the catheter ring 20 is generally composed of non-adhesive silicone that is soft and flexible and is also latex-free. In other embodiments, the catheter ring 20 may be composed of a non-adhesive soft and flexible rubber, latex, or any other soft and flexible functional material.

In the illustrated embodiment, the tubular portion 22 is also composed of non-adhesive silicone of two different densities, for forming the firm portion 30 and the soft portion 28. In other embodiments, the tubular portion 22 may be composed of rubber, latex, or any other functional material. In yet other embodiments, the tubular portion 22 may be composed of silicone, or another material, of only one density so that the tubular portion 22 does not include both a soft portion 28 and a firm portion 30. Rather, the tubular portion 22 in such an embodiment only includes one section composed of a material of a nearly uniform density. The tubular portion 22 and the catheter ring 20 may be composed of the same material or different materials.

The elastic strap 14 includes a first end 38 fixedly or removably attached to the catheter ring 20 and a second end 40 coupled to a side flap 34 attached to the catheter ring 20. The slide flap 34 includes a slot 36 for coupling to the elastic strap 14, as explained in greater detail below.

The second end 40 of the elastic strap 14 may attach to itself in a plurality of ways. For example, as shown in FIGS. 1 and 2, the second end 40 of the elastic strap 14 may have strips of Velcro® so as to couple an edge 42 of the second end 40 to an intermediate portion 44 of the second end 40 that does not extend through the slot 36. FIGS. 3 and 4 illustrate the second end 40 of the elastic strap 14 including a hook-and-loop fastener such as Velcro®, as described above, but also with a plurality of openings 46 in the intermediate portion 44 (i.e., the portion of the elastic strap 14 that does not extend through the slot 36) and a hook 48 on the edge 42 of the second end 40. As illustrated in FIG. 4, the hook 48 can be inserted through one of the plurality of openings 46 to provide a secure coupling at the second end 40 of the elastic strap 14.

Referring to the embodiment of FIG. 5, the second end 40 of the elastic strap 14 includes a plurality of catches 50 and a plurality of openings 52. One or more catches of the plurality of catches 50 may be inserted into associated openings 52 to attach the second end 40 of the elastic strap 14 to itself. The plurality of catches 50 may be positioned on one of the intermediate portion 44 of the elastic strap 14 or the portion of the elastic strap 14 that extends through the slot 36 (i.e., adjacent the edge 42), with the plurality of openings 52 positioned on the other of the intermediate portion 44 or the portion that extends through the slot 36 so as to couple the second end 40 of the elastic strap 14 to itself around the side flap 34.

The embodiment of FIG. 6 illustrates the second end 40 of the elastic strap 14 having a plurality of button snaps 54 to attach the second end 40 of the elastic strap 14 to itself. Each button snap 54 includes a clasp 56 and a fastener 58. The clasps 56 and the fasteners 58 are positioned on either the second end 40 of the elastic strap 14 similar to the plurality of catches 50 and the plurality of openings 52 described above. The second end 40 of the elastic strap 14 may also be attached to itself in other ways not described herein.

FIG. 7 illustrates another embodiment of the condom catheter in which the elastic strap 14 is not directly attached to the catheter ring 20. Rather, each end 38, 40 of the elastic strap 14 is coupled to two loops 62 on the catheter ring 20. As similarly described above in regard to the side flap 34 and the slot 36, the ends 38, 40 of the elastic strap 14 couple back onto themselves after passing through the loops 62. The ends 38, 40 as illustrated are coupled to themselves via Velcro®, however, any coupling medium or component(s) described herein may be used. In other embodiments, any component, e.g., a partial loop, hook, or extension, that presents an anchor point for the ends 38, 40 of the strap 14 to couple back on themselves, can also be used for the illustrated loops 62.

In operation, the condom catheter 10 is secured to the patient to provide a fluid pathway from the urethra to the urine collection bag 16. The catheter ring 20 is positioned around the penis P, near the base of the penis P so that the tubular portion 22 encompasses the remainder of the shaft of the penis P, as illustrated by FIG. 2. The soft portion 28 of the tubular portion 22 provides a comfortable yet tight and form-fitting relationship so that urine is substantially blocked, obstructed, hindered, or otherwise impeded from leaving the tubular portion 22 except through the opening 26. A tube 18 is secured to the tip 32 of the tubular portion 22 to provide a fluid connection between the tubular portion 22 and the urine collection bag 16, as illustrated in FIG. 1. The urine collection bag 16 may be secured to one of the patient's legs, to the side of a hospital bed, or to any other functional location.

The elastic strap 14 extends from the catheter ring 20 at the first end 38 and is wrapped around the torso T of the patient above the hips H and brought back adjacent the condom portion 12 so that the second end 40 of the elastic strap 14 may be secured through the slot 36 of the side flap 34. In some embodiments, the elastic strap 14 has an amount of slack or extra length that is wrapped around the penis P one or more times, as illustrated in FIG. 2 to provide a more secure fit between the condom portion 12 and the penis P. In other embodiments, the elastic strap 14 is not wrapped around the penis P.

After wrapping the slack of the elastic strap 14 around the penis P, the edge 42 of the second end 40 of the elastic strap 14 is inserted through the slot 36 of the side flap 34 and removably secured back onto itself. As explained above, the elastic strap 14 may be secured to itself in a plurality of ways. In other embodiments the second end 40 is removably secured directly to the side flap 34.

Various features and advantages of the disclosure are set forth in the following claims.

What is claimed is:

1. A catheter comprising:
a condom portion including a catheter ring and a tubular portion defining an opening; and
an elastic strap comprising a singular body including a first end and a second end,
wherein the first end of the elastic strap is configured for coupling to the catheter ring, and
wherein the second end of the elastic strap is configured for coupling to the catheter ring,
wherein the elastic strap has a singular, continuous, uninterrupted length between the first and second ends configured for coupling to the catheter ring and is configured to wrap around the user's waist only,
wherein a first segment of the elastic strap is configured to cross over a second segment of the elastic strap at a lower abdomen when the first end and second end of the elastic strap are coupled to the catheter ring, and
wherein the elastic strap is configured to:
extend from a first side of the catheter ring across the lower abdomen to a first side of the waist opposite the first side of the catheter ring;
extend around a lower back of the user to a second side of the waist opposite the first side thereof; and
extend around the second side of the waist crossing the lower abdomen toward a second side of the catheter ring opposite the first side.

2. The catheter according to claim 1 further comprising:
a first loop positioned on the catheter ring, and
a second loop positioned on the catheter ring,
wherein the first end of the elastic strap is configured for coupling to the first loop, and
wherein the second end of the elastic strap is configured for coupling to the second loop.

3. The catheter according to claim 2, wherein the first loop and the second loop are separated by approximately 180 degrees around the catheter ring.

4. The catheter according to claim 3, wherein each of the first end and the second end of the elastic strap includes a first portion and a second portion,
wherein the second portion of the first end of the elastic strap is extendable through the first loop for removable attachment to the first portion of the first end of the elastic strap, and
wherein the second portion of the second end of the elastic strap is extendable through the second loop for removable attachment to the first portion of the second end of the elastic strap.

5. The catheter according to claim 4, wherein each first portion of the first and second ends of the elastic strap is removably attachable to each respective second portion of the first and second ends of the elastic strap by a hook-and-loop fastener.

6. The catheter according to claim 4, wherein each first portion of the first and second ends of the elastic strap is removably attachable to each respective second portion of the first and second ends of the elastic strap by button snaps.

7. The catheter according to claim 4, wherein each first portion of the first and second ends of the elastic strap is removably attachable to each respective second portion of the first and second ends of the elastic strap by a plurality of hooks and a plurality of openings.

8. The catheter according to claim 4, wherein each respective second portion of the first and second ends of the elastic strap includes a hook, and wherein each first portion of the first and second ends of the elastic strap includes a plurality of openings configured to receive the hook.

9. The catheter according to claim 1 wherein the first segment of the elastic strap is configured to cross over the second segment of the elastic strap adjacent to the catheter ring.

10. The catheter according to claim 1, wherein the tubular portion includes a first section and a second section, the second section comprising a material of a different density than that of the first section.

11. The catheter according to claim 10, wherein the first section is nearer the catheter ring than the second section, and wherein the density of the second section is greater than the density of the first section.

12. The catheter according to claim 11, wherein the tubular portion includes a diameter that tapers to the opening.

13. The catheter according to claim 12, wherein the first section extends from the catheter ring to the point on the tubular portion at which the diameter begins to taper to the opening.

14. The catheter according to claim 1, wherein the catheter ring is expandable.

15. The catheter according to claim 1, wherein the tubular portion is made of a non-adhesive silicone.

16. A method of using a catheter, comprising the steps of:
providing a catheter, the catheter comprising:
a condom portion including a catheter ring and a tubular portion defining an opening; and
an elastic strap comprising a singular body including a first end and a second end,
wherein the first and second ends of the elastic strap are configured for coupling to the catheter ring,
wherein the elastic strap has a singular, continuous, uninterrupted length between the first and second ends configured for coupling to the catheter ring, and
wherein the elastic strap is configured to wrap around the user's waist only;
inserting a penis into the condom portion of the catheter;
coupling the first end of the elastic strap to the catheter ring on a first side;
extending the elastic strap above a first hip bone of the user and around a first side of a waist of the user, wherein the first side of the waist is opposite to the first side of the catheter ring to which the first end of the elastic strap is attached;
wrapping the elastic strap around a lower back of the user;
extending the elastic strap around a second side of the waist of the user opposite the first side and above a second hip bone opposite the first hip bone, wherein a first segment of the elastic strap crosses over a second segment of the elastic strap; and
coupling the second end of the elastic strap to the catheter ring on a second side opposite the first side.

* * * * *